(12) United States Patent
Georgopoulos

(10) Patent No.: US 10,043,129 B2
(45) Date of Patent: Aug. 7, 2018

(54) FUNCTIONAL ASSESSMENT OF A NETWORK

(75) Inventor: Apostolos Georgopoulos, Minneapolis, MN (US)

(73) Assignees: Regents of the University of Minnesota, Minneapolis, MN (US); Department of Veterans Affairs, Washington, DC (US)

(*) Notice: Subject to any disclaimer, the term of this patent is extended or adjusted under 35 U.S.C. 154(b) by 876 days.

(21) Appl. No.: 13/312,332

(22) Filed: Dec. 6, 2011

(65) Prior Publication Data

US 2012/0143038 A1    Jun. 7, 2012

Related U.S. Application Data

(60) Provisional application No. 61/420,093, filed on Dec. 6, 2010.

(51) Int. Cl.
*G06N 3/04* (2006.01)
*A61B 5/04* (2006.01)
*A61B 5/00* (2006.01)

(52) U.S. Cl.
CPC .......... *G06N 3/04* (2013.01); *A61B 5/04008* (2013.01); *A61B 5/4064* (2013.01); *A61B 5/7264* (2013.01); *A61B 5/6803* (2013.01)

(58) Field of Classification Search
CPC . A61B 5/04008; A61B 5/4064; A61B 5/6803; A61B 5/7264
USPC ..................... 600/409, 544; 128/925; 702/19
See application file for complete search history.

(56) References Cited

U.S. PATENT DOCUMENTS

| | | | | |
|---|---|---|---|---|
| 4,188,956 A | * | 2/1980 | John | 600/544 |
| 4,846,190 A | * | 7/1989 | John | 600/544 |
| 6,129,665 A | * | 10/2000 | Zanin | 600/346 |
| 7,110,582 B1 | * | 9/2006 | Hay | 382/128 |
| 8,306,942 B2 | | 11/2012 | Chen et al. | |
| 2005/0124863 A1 | | 6/2005 | Cook | |

(Continued)

OTHER PUBLICATIONS

Selinger et al., "Measuring synchronization in neuronal networks for biosensor applications", Biosensors and Bioelectronics, vol. 19, Issue 7, Feb. 15, 2004, pp. 675-683.*

(Continued)

*Primary Examiner* — Katherine Fernandez
(74) *Attorney, Agent, or Firm* — Dicke, Billig & Czaja, PLLC

(57) ABSTRACT

A computer-implemented method for performing a functional assessment of a network is disclosed. The network includes a plurality of interacting network elements. The method includes measuring a state of each of the elements at a plurality of time instances, thereby determining a plurality of state values associated with each of the elements, and calculating for each element an associated median value representing a median of the state values associated with that element. The method further includes identifying for each time instance a first total number of elements with an associated state value at that time instance that is above its median value, and a second total number of elements with an associated state value at that time instance that is below its median value, and determining whether the network has departed from an equilibrium state based on the first total number and the second total number for each time instance.

16 Claims, 14 Drawing Sheets

(56) References Cited

U.S. PATENT DOCUMENTS

| | | | |
|---|---|---|---|
| 2005/0170528 | A1 | 8/2005 | West et al. |
| 2005/0209785 | A1 | 9/2005 | Wells et al. |
| 2007/0269804 | A1 | 11/2007 | Liew et al. |
| 2008/0091118 | A1* | 4/2008 | Georgopoulos ............ 600/544 |
| 2008/0103996 | A1 | 5/2008 | Forman et al. |
| 2008/0133141 | A1 | 6/2008 | Frost |
| 2008/0228677 | A1 | 9/2008 | Kenedy et al. |
| 2009/0318773 | A1 | 12/2009 | Jung et al. |
| 2011/0270348 | A1* | 11/2011 | Goetz ........................ 607/45 |

OTHER PUBLICATIONS

Georgopoulos, Apostolos P., et al., Synchronous neural interactions assessed by magnetoencephalography: a functional biomarker for brain disorders, Journal of Neural Engineering, 2007, pp. 349-355, 4, IOP Publishing Ltd., UK.

Georgopoulos, Apostolos P., et al., The Synchronous neural interactions test as a functional neuromarker for post-traumatic stress disorder (PTSD): a robust classification method based on the bootstrap, Journal of Neural Engineering, 2010, pp. 1-7, IOP Publishing Ltd., UK.

"Dynamic nonlinear modeling of neural ensemble activity", Program of BMSR Workshop at the EMBC 2011, Aug. 30, 2011, 2 pgs.

PCT Search Report for PCT/US10/28504 dated May 7, 2010, 8 pgs.

\* cited by examiner

FUNCTIONAL ASSESSMENT OF A NETWORK

CROSS-REFERENCE TO RELATED APPLICATION

This application claims priority under 35 U.S.C. § 119(e) to U.S. Provisional Patent Application Ser. No. 61/420,093 filed on Dec. 6, 2010, entitled FUNCTIONAL ASSESSMENT OF A NETWORK, and incorporated herein by reference.

BACKGROUND

The brain is one example of a network (i.e., a neural network). Neural disorders are ultimately manifested as abnormal interactions in neural networks controlling specific functions. Very little is known about the workings of neural networks. Although a wealth of knowledge has been accumulated concerning the morphology, biochemistry, electrophysiology, synaptic activity and development of individual neurons, much less is known about how they work together in small or larger ensembles to accomplish their function. There are three main reasons for this lack of knowledge. First, there has been so much preoccupation with individual cells and chemicals (e.g., neurotransmitters) that neural networks as carriers of information have been overshadowed. Second, technology for studying neural networks has been largely absent. And third, the theoretical background for studying neural networks has not yielded any rigorous and robust measure of neural network function.

SUMMARY

One embodiment provides a computer-implemented method for performing a functional assessment of a network. The network includes a plurality of interacting network elements. The method includes measuring a state of each of the elements at a plurality of time instances, thereby determining a plurality of state values associated with each of the elements, and calculating for each element an associated median value representing a median of the state values associated with that element. The method further includes identifying for each time instance a first total number of elements with an associated state value at that time instance that is above its median value, and a second total number of elements with an associated state value at that time instance that is below its median value, and determining whether the network has departed from an equilibrium state based on the first total number and the second total number for each time instance.

DETAILED DESCRIPTION

Figure 1:
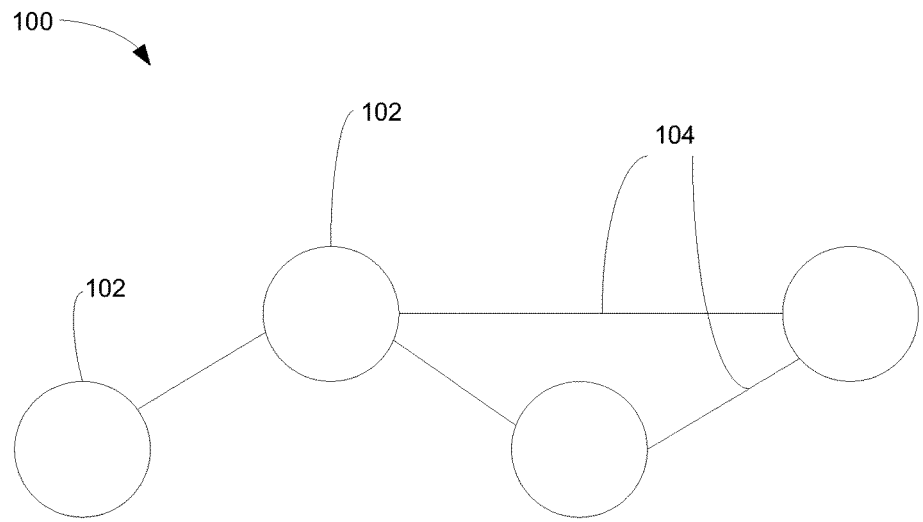
FIG. 1 is a diagram illustrating a network according to one embodiment.

FIG. 1 is a diagram illustrating a network 100 according to one embodiment. Network 100 includes a plurality of network elements 102 and a plurality of links 104 that interconnect the elements 102. The links 104 according to one embodiment represent interactions that occur between elements 102. One embodiment provides a system and method for assessing the functional status of a network, such as network 100. There are many different types of networks, and the entities represented by elements 102 will vary depending on the type of network. A few examples of networks include the brain (composed of neurons), society at large (composed of people), special-interest groups (e.g., composed of members of a chat room), organizations (e.g., composed of members of a university, government agency, business, etc.), cells (composed of molecules), etc. Typically, networks are characterized by massive interactions among their constituent elements. For example, the essence of brain function lies in the workings of networks of interacting neurons.

At present, there is no general measure to assess the functional status of a network. Current approaches focus on aggregate measures (e.g., means, variance, distributions, etc.) with little or no attention to the interactions between the members of the network, and yet the dynamics of the network and its output (e.g., thoughts, actions, wars, sales, etc.) may crucially depend on and reflect those interactions. It is a challenge to derive a single measure by which to characterize intrinsic network function.

Figure 2:
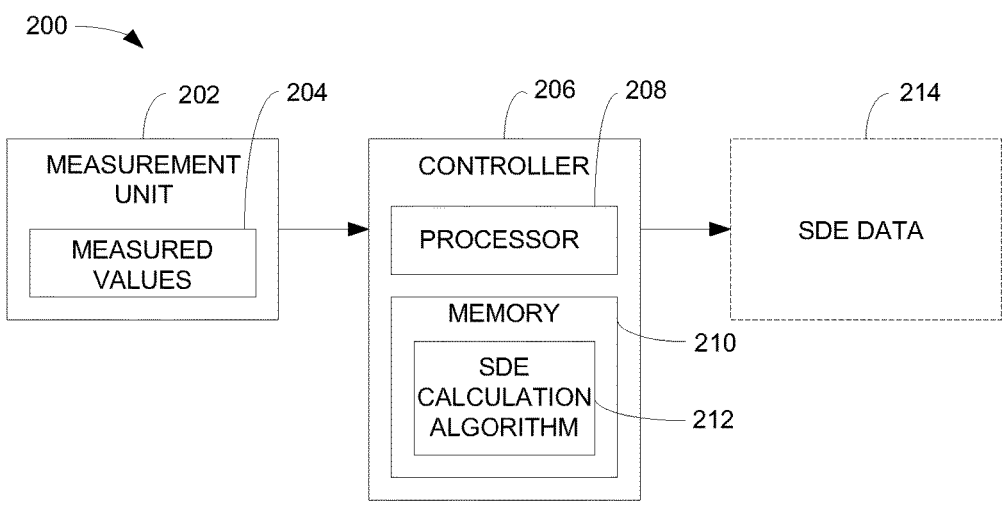
FIG. 2 is a block diagram illustrating a system for assessing the functional status of a network according to one embodiment.

FIG. 2 is a block diagram illustrating a system 200 for assessing the functional status of a network according to one embodiment. System 200 includes a measurement unit 202 and a controller 206. Measurement unit 202 is configured to measure a state or property of elements in a network at a plurality of instances in time, thereby generating a plurality (e.g., a time series) of measured values 204 for each such element. Measurement unit 202 provides the measured values 204 to controller 206 for processing.

In one embodiment, measurement unit 202 includes at least one multi-electrode array (MEA) that records neural activity of a network, such as cultured embryonic tissue from a rat brain. The MEAs used in one embodiment have dimensions of 1.4×1.4 mm and contain an array of 60 electrodes on a flat surface, surrounded by a circular wall that creates a well around the electrodes. The electrodes are embedded in the MEA surface and are arranged in a square grid. The electrodes are titanium nitride disks of 30 μm in diameter, spaced at 200 μm intervals. To record the activity of neurons, the MEAs are removed from an incubator and placed in pre-heated (e.g., 37° C.) amplifiers, which are in an enclosed plastic Faraday box to restrict light. During each day of data collection according to one embodiment, neural activity is recorded continuously for 5 minutes at 1 kHz/channel, and then again for 1 minute at 20 kHz/channel. In one embodiment, measurement unit 202 includes two MEA recording systems for a total of 60×2=120 simultaneous recording sites.

In another embodiment, measurement unit 202 is configured to generate biomagnetism data. Biomagnetism refers to the measurement of magnetic fields from sources within the body. These fields are produced by magnetic materials or ionic currents associated with biological activity. One application in the field of biomagnetism involves the measurement of human brain activity, such as with a magnetoencephalography (MEG) device. A MEG device measures magnetic fields produced by electrical activity in the brain. In one embodiment, measurement unit 202 includes a MEG device with tens or hundreds of sensors, such as "SQUIDS". A SQUID (Superconducting Quantum Interference Device) is a superconducting device for detecting magnetic fields. A SQUID, along with its associated feedback electronics, provides an output voltage proportional to the magnetic flux applied to its detection coil. In one embodiment, the MEG device includes a helmet configured for "whole head" analysis of a subject (e.g., a human subject). When a group of neurons (for example, 10,000 or more) are activated together, the magnetic field produced by the net current may be detected by the coils of the SQUIDS in the MEG device. The MEG device may be used to generate data for a synchronous neural interactions (SNI) test, which assesses dynamic brain function by evaluating neural interactions at high temporal resolution. The test involves the use of zero-lag partial correlations between prewhitened MEG time series. It will be understood that the type of device or devices used for measurement unit 202 will vary depending upon the type of network being evaluated.

Controller 206 is configured to receive and process the measured values 204 generated by measurement unit 202. In one embodiment, controller 206 comprises a computing system or computing device that includes at least one processor 208 and memory 210. Depending on the exact configuration and type of computing device, the memory 210 may be volatile (such as RAM), non-volatile (such as ROM, flash memory, etc.), or some combination of the two. The memory 210 used by controller 206 is an example of computer storage media (e.g., computer-readable storage media storing computer-executable instructions for performing a method). Computer storage media used by controller 206 according to one embodiment includes volatile and nonvolatile, removable and non-removable media implemented in any suitable method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that can be used to store the desired information and that can be accessed by controller 206.

In the illustrated embodiment, memory 210 stores a simultaneous departure from equilibrium (SDE) calculation algorithm 212. Processor 208 is configured to execute the SDE calculation algorithm 212, which results in the generation of SDE data 214 based on the received measured values 204. In one embodiment, system 200 is configured to perform a functional assessment of a dynamic network. The assessment according to one embodiment is based on classical thermodynamics, and in particular the concept of equilibrium. For a given network, system 200 is configured to compute the instantaneous global departure from equilibrium, which is indicative of the stability of the network. This measure is referred to herein as a simultaneous departure from equilibrium (SDE) value. SDE according to one embodiment is a single measure for characterizing intrinsic network function, and quantifies the instantaneous departure from equilibrium as the ratio of network elements with activity above or below their average activity. SDE can be regarded as a measure of the functional vitality or quality of the network, or of the magnitude of cooperation among constituent subnetworks.

Controller 206 according to one embodiment is configured to compute SDE values as follows. Assume that N represents a network consisting of k elements E. The state (e.g., an intensity value) of each element E is measured by measurement unit 202 at a regular time interval τ. The state values are represented in FIG. 2 by measured values 204. For the duration T, there are M=T/τ samples or state values available for each element: E(t=0), E(t=1), E(t=2), ..., E(t=M). Controller 206 calculates the median of the time series E(t) for each element, which is represented by MED[E(t)]. For each time instant t=0, 1, 2, 3, ..., M, controller 206 compares the value of E(t) to its median, MED. The value of E(t) can be above (represented by A), below (represented by B), or equal to MED[E(t)]. In the last case (when E(t)=MED[E(t)]), E(t) is reassigned randomly in one embodiment to A or B. For every instant t, controller 206 computes the sum of A's and B's [SUM($A_t$) and SUM($B_t$)] across E(t)'s. Then, in one embodiment, controller 206 calculates the measure SDE(t) (which is represented in FIG. 2 by SDE data 214) as shown in the following Equation I:

$$\text{SDE}(t) = \text{abs}\{\log\,[\text{SUM}(A_t)/\text{SUM}(B_t)]\}. \qquad \text{EQUATION I}$$

If SUM($A_t$)=SUM($B_t$), then SUM($A_t$)/SUM($B_t$)=1, and SDE(t)=log(1)=0, which indicates that the network is at equilibrium. If SUM($A_t$) does not equal SUM($B_t$), then SDE(t) is different from zero, and the magnitude of its value reflects the distance of departure from equilibrium. Since SUM($A_t$) or SUM($B_t$) can be zero, the SDE(t) calculation in Equation I is adjusted in one embodiment by adding a constant, as shown in the following Equation II:

$$\text{SDE}(t) = \text{abs}\{\log\,[\text{SUM}(A_t)/\text{SUM}(B_t)] + 1\} \qquad \text{EQUATION II}$$

Finally, the average SDE=SUM($SDE_t$)/M across M time samples of t for duration T, is calculated by controller 206 and provides a measure of the varying, global interactions in the network. In addition, the detailed time course of SDE(t) and its spectrum provide fine-grain information about the time- and frequency-varying aspects of these interactions. SDE is a general-purpose assessment of the global interactions in any network, either instantaneous or averaged over time. Since these interactions are the essence of network function, SDE is a key measure assessing that essence.

Figure 3:
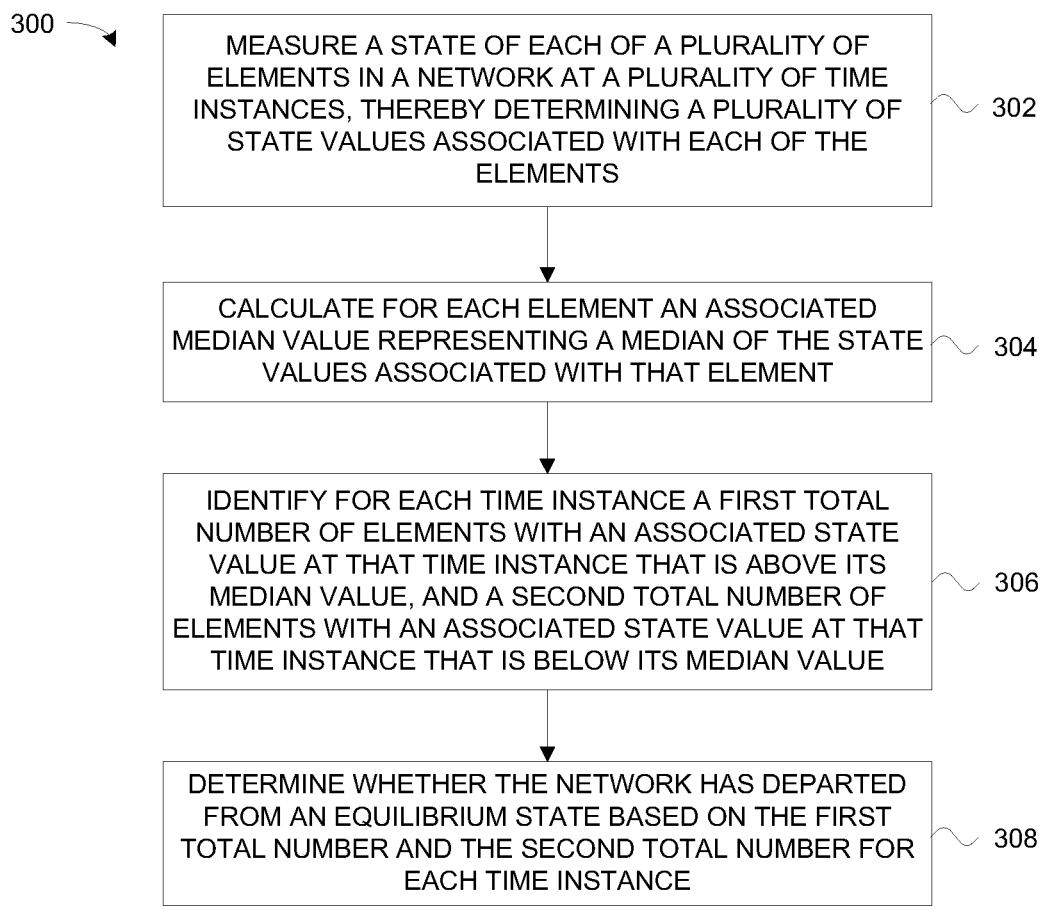
FIG. 3 is a flow diagram illustrating a method for performing a functional assessment of a network according to one embodiment.

FIG. 3 is a flow diagram illustrating a method 300 for performing a functional assessment of a network according to one embodiment. In one embodiment, method 300 is a computer-implemented method, and system 200 (FIG. 2) is configured to perform method 300. In one embodiment, the network being assessed by method 300 includes a plurality of interacting network elements. At 302 in method 300, measurement unit 202 measures a state of each of the elements at a plurality of time instances, thereby determining a plurality of state values associated with each of the elements. At 304, controller 206 calculates for each element an associated median value representing a median of the state values associated with that element. At 306, controller 206 identifies for each time instance a first total number of elements with an associated state value at that time instance that is above its median value, and a second total number of elements with an associated state value at that time instance that is below its median value. At 308, controller 206 determines whether the network has departed from an equilibrium state based on the first total number and the second total number for each time instance.

The calculating (304), identifying (306), and determining (308) in method 300 according to one embodiment are performed by at least one processor 208. In one embodiment, the determining whether the network has departed from an equilibrium state at 308 in method 300 includes calculating for each time instance a departure from equilibrium value based on the first total number and the second total number, wherein a magnitude of the departure from equilibrium value represents a distance of departure from equilibrium. In one embodiment, the calculating for each time instance a departure from equilibrium value includes dividing the first total number by the second total number, and calculating a logarithm of a result of the division. In one embodiment, the calculating for each time instance a departure from equilibrium value further includes adding a constant value to a result of the logarithm, thereby generating a sum, and calculating an absolute value of the sum.

One embodiment provides a system 200 that uses multi-electrode array (MEA) technology and SDE calculations for the noninvasive and lengthy assessment of brain function in vitro. Neural activity is recorded from many sites (e.g., 60 in one embodiment) simultaneously for a long time (e.g., weeks or months). This system 200 is attractive for studying neural networks in action, the effects of various interventions on them (e.g., drugs, stimulation, etc.), neural plasticity, etc. In addition, the system 200 can be used to study brain function in transgenic animals that show behavioral alterations much later in life. Such animals comprise all of those with mutations/genetic interventions that affect the brain, including, for example, mouse models of AD, epilepsy, Huntington's disease, mental retardation (fragile X), etc., to name but a few. These brains may show specific abnormalities in network function which, with the techniques disclosed herein, could be detected, characterized, and quantified at the embryonic stage of development (i.e., long before behavioral abnormalities are manifested).

The techniques described herein have been applied to the neural network activity observed in brain cultures in five experiments: four experiments to assess in real time the effect of Apolipoprotein E4 (a known risk factor for Alzheimer's disease) on the functional interactions of the networks in vitro, and a fifth experiment to assess differences in the functional interactions of neural networks in vitro from mouse models of Fragile X syndrome (a genetic abnormality associated with autism and mental retardation in humans). In the first experiment, embryonic tissue was cultured from a rat brain in a special dish that included a multi-electrode array, and neural activity of the neurons in the dish was recorded simultaneously from 60 electrodes embedded in the dish. Four arrays (240 recordings) were used as controls and four arrays (240 recordings) were subjected to a treatment by adding a lipoprotein subfraction from a human subject with the Apolipoprotein E4/E4 (ApoE4/E4) homozygotic genotype. The concentration of apoE4 was 7 micrograms/ml. A highly statistically significant increase in SDE was observed in the ApoE4 treated networks, as compared to the controls. This indicates a more correlated network with consequent reduction in its degrees of freedom, hence a more functionally constrained (i.e. impaired) network.

In the second experiment, the same procedure was followed, but five arrays (300 recordings) were used as controls and five arrays (300 recordings) were subjected to a treatment by adding recombinant ApoE4 to embryonic rat brain cultures (at a concentration of 10 micrograms/ml of serum-free media). Recordings were obtained for 21 days. Similarly to the results of the first experiment above, a highly statistically significant increase in SDE was observed in the ApoE4 treated networks, as compared to the controls.

In the third experiment, embryonic brain cultures from mice brains were employed. Four arrays (240 recordings) were used as controls and four arrays (240 recordings) were subjected to a treatment by adding recombinant ApoE4 (at a concentration of 10 micrograms/ml of serum-free media). Recordings were obtained for 19 days. Similarly to the results of the experiments above, a highly statistically significant increase in SDE was observed in the ApoE4 treated networks, as compared to the controls.

In the fourth experiment, neuroblastoma cell cultures were used to test the effect of recombinant apoE4. This is a pure cell line and a totally different platform for this testing. Three arrays (180 recordings) were used as controls and three arrays (180 recordings) were subjected to a treatment by adding recombinant ApoE4 (at a concentration of 10 micrograms/ml of serum-free media). Recordings were obtained for 7 days. Similarly to the results of the experiments above, a highly statistically significant increase in SDE was observed in the ApoE4 treated networks, as compared to the controls.

Altogether, these results, from very different experiments, demonstrate a consistent effect of Apoe4 in four different combinations of experimental conditions (rat brains/human ApoE4/E4, rat brains/recombinant ApoE4, mouse brains/recombinant ApoE4, neuroblastoma cell cultures/recombinant ApoE4), namely a hyper-correlated network. Studies are currently proceeding using genetically altered mouse brains (e.g., ApoE deficient mice) to detect network abnormalities very early, and to predict behavioral abnormalities usually manifested after several months postnatally. This study involves investigating the possibility that genetic abnormalities in altered brains are manifested as disturbances in neural network function at the embryonic stage of development, and that such network disturbances will differ depending on the genetic alteration.

Initial validation of this idea has been obtained in the fifth experiment by studying SDE in two groups of mice, one control and one genetically altered to model Fragile X syndrome. Six arrays (360 recordings) were used for the control (same mouse strain) and five arrays (360 recordings) for the Fragile X mouse brains. A highly significant decrease in SDE was found in the Fragile X mice. This indicates hypoperformance and restricted range in network function, and provides an insight into network mechanisms underlying mental retardation.

Finally, studies are planned to use multi-electrode arrays and the techniques described herein to test the effects of drugs on network function. A study is also underway to apply the techniques described herein to stock market data and to data of a number of seismic sensors. The findings in the studies and experiments described above attest to the utility and validity of the techniques described herein.

The techniques described herein may also be used for other applications. A preliminary study involving magnetoencephalography (MEG) biomarkers has been very promising. Specifically, the techniques described herein have been applied on whole-brain MEG recordings in humans, with good success in discriminating and classifying brain diseases. This application is particularly useful because the SDE can be computed from any MEG data and is device-independent, which means that it can be applied to any MEG system. To validate the utility of the SDE in this domain, we compared the SDE distributions of the following brain diseases: Alzheimer's disease (N=96 patients), mild cognitive impairment (N=35), schizophrenia (N=20), Sjogren's syndrome (N=32), chronic facial pain (temporomandibular joint disorder) (N=9), multiple sclerosis (N=50), post-traumatic stress disorder (N=105), chronic alcoholic (N=43), autism (N=7) and healthy controls (N=604). We carried out all pairwise comparisons using the robust, nonparametric Kolmogorov-Smirnov test. We found that all the SDE distributions differed highly significantly from one another in all comparisons (P<0.001). In addition, we found a hypersynchrony in the AD distribution of SDE (with respect to controls), which is in the same direction as the one found in brain cultures after the addition of apoE4/apoE4 (see above). Since this polymorphisms is a known risk factor for AD, the similarity of SDE shift in both cultures and brains is remarkable. These results further validate the SDE as a powerful tool for assessing network function.

The techniques described herein have many possible applications, including the following: (1) Assessing the function of neural networks in vitro (drug effects, disease, other interventions), as a test bed for research and development; (2) assessing neural network function in vivo (MEG, EEG, functional biomarkers, drug effects, etc.); (3) assessing the function of any network (people, organizations, departments, political parties, student classrooms, stock market, etc.); (4) assessing customer networks in marketing research, web search data, etc.; the derived information may be used as feedback to change/improve/modify networks (e.g., in social/marketing applications); and (5) assessing natural conditions, such as seismic readings in earthquake prediction and weather readings in inclement weather prediction (e.g. tornadoes).

Additional MEA Testing

Additional MEA testing has been performed that validates SDE as a measure for the overall assessment of network status. Electrical activity from four developing embryonic brain cultures (4-40 days in vitro) was recorded using multielectrode arrays (MEAs) with 60 embedded electrodes. Daily recordings lasted 60 s and the electrical signal was sampled at 20 kHz. Data were filtered for local field potentials (LFP, 0.7-170 Hz) and downsampled to 1 ms to yield a matrix of time series consisting of 60 electrode×60,000 time samples per electrode per day per MEA. Each electrode time series was converted to white noise by applying a ARIMA model and taking the residuals (i.e. innovations). Three analyses were then performed on the prewhitened data. First, a crosscorrelation (CC) analysis (±25 1-ms-long lags) revealed systematic changes in CC with lag, day in vitro (DIV) and inter-electrode distance. Specifically, (i) positive CCs were 1.76× more prevalent and 1.44× stronger (absolute value) than negative ones, and (ii) the strength of CC increased with DIV and decreased with lag and inter-electrode distance. Second, a network equilibrium analysis was based on the instantaneous (1-ms resolution) log ratio of the number of electrodes that were above or below their median (i.e., simultaneous departure from equilibrium or SDE). This analysis revealed a systematic increase of SDE with DIV. Finally, a temporal analysis (100-ms resolution) between the overall strength of neural interactions (average absolute CC, $|\overline{CC}|$) and the network's departure from equilibrium revealed a feedforward-feedback system, with the neural interactions driving the network out of equilibrium by increasing SDE, while SDE provides, in turn, negative feedback on $|\overline{CC}|$. These findings contribute to the utility of MEAs as a useful tool for studies of neural network development and validate SDE as a measure for the overall assessment of network status. Additional details regarding this testing are provided below.

1. Introduction

Although a wealth of knowledge has been accumulated concerning the morphology, biochemistry, electrophysiology, synaptic activity and development of individual neurons, there is little information on how neurons work together in small or large ensembles to form dynamic neural networks. Correlated patterns of spontaneous neuronal activity have been observed throughout the nervous system within the early stages of development. Particularly, in vivo electrophysiological studies in fetal and neonatal retina showed that individual retinal ganglion cells exhibit spontaneous bursts of action potentials, which are synchronized between nearby cells. However, this pattern of activity disappears in adult rats. In addition, in vivo studies have revealed similar patterns of spontaneous bursting activity in the developing lateral geniculate nucleus (LGN). There is a great deal of evidence that these patterns of activity have an important role in the development of neuronal networks in the visual system through selective synapse stabilization. However, despite these studies in the retina and LGN, little is known about the in vivo pattern of spontaneous activity and the interactions between neuronal cells in other areas of the nervous system. Recent technological advancements in MEA technology have permitted in vitro experiments in developing cortical networks to study the neuronal activity and the spatial and temporal interactions between neurons in real time, as well the effect of various interventions on the cell cultures (e.g., stimulation). Electrophysiological recordings in MEAs have shown that cortical networks exhibit patterns of spontaneous neuronal activity associated with the developmental stage of the culture. It seems that cells build synaptic connections with each other during the first days of culturing, forming subnetworks and exhibiting spontaneous electrical activity. Once mature, MEA cultures exhibit strong interconnections and synchronized bursts of activity across the entire network separated by few seconds of quiescence.

In the present study, crosscorrelation analysis was performed on stationary, non-autocorrelated LFP time series obtained after prewhitening. In addition, the scalar measure, SDE, was used to provide an estimate of the synchronous fluctuations of the network on a millisecond-by-millisecond basis. SDE is based on the thermodynamic concept of equilibrium and quantifies the instantaneous departure from it as the ratio of neurons with activity above or below their median activity. By averaging the SDE across the whole period of recording, a single measure is obtained that describes the behavior of the neural network as a whole.

2. Materials and Methods

2.1. Cell Cultures

Cortical cells were isolated by dissociation from cortical tissue of embryonic day 18 Spraque/Dawley rats (BrainBits, Springfield, Ill.) and plated on MEAs (MutliChannelSystems, Reutlingen, Germany). To dissociate the cells, the cortical tissue in media (in Neurobasal/B27+0.5 mM Glutamax; Invitrogen, Carlsbad, Calif.) was triturated 10 times, using a 1 ml tip. More neurobasal media (1 ml) were then added to the triturated mixture and the undispersed tissue was allowed to settle to the tube bottom for a period of one minute. The supernatant was then transferred to a new sterile 15 ml tube and spun in a refrigerated centrifuge at 200 g for 1 min. The supernatant was discarded. The pellet was resuspended in 1 ml of Neurobasal media. To estimate the number of cells in the suspension, 10 µl was aliquoted into a tube containing 90 µl 0.4% trypan blue solution (Sigma T8154). Cells were then counted using a hemocytometer. Approximately 250,000 cells in 100 µl of media were pipetted directly onto and around the electrode area of each MEA. Prior to plating, the MEAs were sterilized with UV light for 1 h, and were then incubated with poly-d-lysine (50 µg/ml) for 2 h. Then, the poly-d-lysine solution was removed, the wells were rinsed with sterile water, and the cells transferred to the MEAs. After plating, the MEAs were covered by a Teflon cover and placed in an incubator for 1 h at 37° C. in a humidified incubator containing 5% $CO_2$ to allow the cells to adhere to the MEAs. After this time, the media were removed and replaced with 0.9 ml of fresh, pre-incubated Neurobasal media. Fresh media were made weekly, and one-half of the media (0.45 ml) in each MEA was replaced every 3-4 days.

2.2. Data Acquisition

Each MEA contained 60 electrode sites on a flat surface surrounded by a circular wall that created a well around the electrodes. The electrodes were titanium nitride disks (30 µm in diameter). They were embedded in the surface of the MEA and arranged in a square grid, spaced at 200 µm intervals. To record the activity of the neurons, the MEA was removed from the incubator and placed in a pre-heated (37° C.) amplifier assembly located within a Faraday shielded black metal box. The electrical activity from each electrode was preampliflied using a low-pass filter of 15 kHz, amplified using a band-pass filter of 1 Hz-3 kHz, and then sampled at 20 kHz. The amplification stages and data recording were built in the MEA hardware. Electrical activity from all 60 electrodes from a MEA was recorded daily for 1 min.

2.3. Data Analysis

2.3.1. Local Field Potentials (LFPs)

LFP activity was derived from the data recorded at 20 kHz by applying a second-order band-pass Butterworth filter at 0.7-170 Hz to reject low and high frequencies outside the LFP range. The filtered time series were then downsampled to 1 kHz for further analysis. Thus, the data from each electrode comprised 60,000 time samples. Noisy and saturated electrodes were visually detected and eliminated from further analysis.

2.3.2. Data Preprocessing: Prewhitening the LFP Time Series

Initial inspection of the LFP time series from many electrodes revealed that they were non-stationary with respect to the mean (i.e. with trends) and highly autocorrelated (the variance did not vary much along the series). Since we were interested in assessing the interactions between these series by calculating the crosscorrelation function (CCF), it is required, from first principles, that individual series be rendered stationary and nonautocorrelated for their crosscorrelation to be valid (i.e. not spurious) assessments of these interactions. "Stationarity" implies that statistical parameters do not vary along the time series, i.e. they are invariant under translations of the time axis; and lack of significant autocorrelation is indicated by a practically flat autocorrelogram of the series. By appropriate preprocessing (see below), the time series are converted to white noise, hence the term "prewhitening". For that purpose, the strategy is to model the series and then apply the model and take the residuals; the better the modeling of the series is, the closer the residuals will be to white noise. This prewhitening is commonly achieved in two stages. The first stage is called model identification and consists in identifying the factors that are relevant for the internal structure of the series. The tools for this step consist of inspecting the series and plotting autocorrelation functions, including the raw autocorrelation (ACF) and the partial autocorrelation (PACF).

Based on the data time series plot and the shape of ACF and PACF, a tentative model is suggested with respect to three kinds of basic factors: dependence of a value on previous values ("AutoRegressive, AR" component of the model), presence of time trends ("Integrative, I" component of the model), and dependence of a value on the variation of previous values ("Moving Average, MA" component). This is called ARIMA modeling of a time series (from the capitalized initials of the three model components above). An ARIMA model is concisely described as of (p, d, q) orders, where p denotes the AR orders (i.e. the number of AR lags in the model), d denotes the I orders (i.e. the number of differencing in the model), and q denotes the MA orders (i.e. the number of MA lags in the model).

After a tentative choice of (p, d, q) orders, we proceed in the second stage, namely model parameter estimation. This stage involves computations which are commonly implemented in several statistical packages and which yield coefficients for the AR and MA lags specified. Typical diagnostic checking of the model involves plotting the residuals, their ACF and PACF, ensuring that the AR and MA coefficients are within bounds of stationarity and invertibility, respectively, and calculating some global measures, including the sums of the squares of residuals, Akaike's information criterion, Schwartz's Bayesian criterion, etc. The essential point for this application was not really to model the series perfectly (this could be an ad hoc objective of another study aimed to elucidate the various dependencies in a time series) but to model it adequately enough so that the residuals obtained are stationary and nonautocorrelated. If indeed so, they are retained for the subsequent crosscorrelation analysis; otherwise, the model is further refined iteratively by varying the (p, d, q) orders until this goal is attained.

Let $X_t$ be a LFP time series. Typically, we start with (p=0, d=1, q=0) which involves first-order differencing: $X_t - X_{t-1}$. This aims to remove nonperiodic time trends which are ubiquitous, even in random walks. Periodic trends, if present, say at lag k are removed by differencing at that lag: $X_t - X_{t-k}$. Extensive iterative investigation yielded an ARIMA model of (p=25, d=1, q=1), or (25,1,1) for short, which yielded stationary and nonautocorrelated residuals. These residual series are called "innovations". Given that we used 25 AR orders and first order differencing, the length of the innovations series $\{Q_t\}$ available for further analysis was N=60,000−26=59,974. We used Matlab (R2010b, version 7.11.0.584, 64 bit) to carry out the AMNIA modeling. Our choice of 25 AR orders was dictated by the fact that our crosscorrelation analysis extended up to 25 lags, so we wanted to ensure lack of autocorrelation for those lags.

2.4. Evaluating the Adequacy of ARIMA Model

We used the autocorrelation function of the innovations time series to evaluate the adequacy of the ARIMA (25, 1, 1) model that we applied to the raw LFP series for prewhitening. For that purpose, we calculated the approximate two-sided 5% critical values for the autocorrelation coefficient $\hat{\rho}$(lag) as $\pm 2\sqrt{1/N}$, where N is the length of the innovations series. Then, we counted how many (of the ACF lags) exceeded that criterion. Since we would still expect to find roughly 5% of the lags to have $\hat{\rho}$(lag) lying outside the critical values, even if the innovations series $Q_t$ were random, we considered adequately modeled those series for which the ARIMA (25, 1, 1) yielded innovations $Q_t$ the autocorrelogram of which did not contain more than 2 lags exceeding the 5% criteria above. Using this screening procedure, 92% of the innovations series were retained for the crosscorrelation analysis.

2.5. Crosscorrelations

Crosscorrelations CC between the innovations series $Q_t$ of each pair of electrodes were calculated for ±25 lags, corresponding to ±25 ms. In addition to the lag-based analysis, we also analyzed the zero-lag crosscorrelations $CC^0$ as a special case. Crosscorrelations were z-transformed to stabilize their variance and normalize their distributions:

$$zCC = \frac{1}{2}\ln\frac{1+CC}{1-CC}.$$

2.5.1. Partial Crosscorrelations

Partial correlations at zero lag $PCC^0$ were computed to evaluate relations between two electrodes accounting for separate relations of these electrodes to all other electrodes.

2.6. Equilibrium Analysis of Neuronal Networks

Simultaneous departure from equilibrium (SDE) was used to characterize the intrinsic network function, as follows. The following calculations refer to prewhitened time series. Let K be the number of electrodes from which cell activity has been recorded simultaneously for a period T. We compute the median electrical activity mLFP(k) recorded from each electrode k across the whole period T. We define A(t) and B(t) the number of electrodes that at a given time t have an LFP measurement above or below their median, respectively; if the LFP value of a sample equals the median of the K time series, it is randomly assigned to the "above" or "below" category. At any given time t, the ratio given in the following Equation III is a measure of the simultaneous departure from equilibrium for the whole neuronal network; the expected equilibrium is at A(t)=B(t):

$$r(t) = \frac{A(t)}{B(t)} \quad \text{EQUATION III}$$

To account for the possibility that all electrodes may go above or below their median values at a given time t, and thus avoid division by zero, we add a constant as shown in the following Equation IV:

$$r'(t) = \frac{A(t)+1}{B(t)+1} \quad \text{EQUATION IV}$$

Next, we take the log of this ratio to make the distribution symmetric. Since the sign of r'(t) is irrelevant with respect to the preponderances of above or below counts, we take its absolute value as shown in the following Equation V:

$$r''(t) = \left|\log_2\left(\frac{A(t)+1}{B(t)+1}\right)\right| \quad \text{EQUATION V}$$

Next, to account for variation in the number of valid recording electrodes, we normalize r''(t) with respect to its maximum value $r_{max}$, where $r_{max}$ is defined as shown in the following Equation VI:

$$r_{max} = |\log_2(K+1)| \quad \text{EQUATION VI}$$

Hence, we define the simultaneous departure from the equilibrium at a given time point t as shown in the following Equation VII:

$$SDE(t) = \frac{r''(t)}{r_{max}} \quad \text{EQUATION VII}$$

Finally, we compute the average $\overline{SDE}$ as the mean of all SDE (t) calculated for each session and MEA. This measure provides an estimate of the average level of synchronous fluctuations of the K prewhitened LFP series away from their session median.

2.7. Statistical Analyses

Matlab R2010b, version 7.11.0.584 (64 bit) and the IMSL statistical library FORTRAN (Compaq Visual Fortran Professional Edition, version 6.6B) were used for all computations using personal computers. Standard statistical analyses were performed using the IBM SPSS statistical package for Windows (version 19).

3. Results 3.1. General

Four MEAs were cultured for 40 DIV; recordings were obtained in consecutive days, beginning at DIV 4, for a total of 37 days. Neuronal "avalanches" were observed at later DIVs, but they were effectively prewhitened, as evidenced by the flat autocorrelations of the innovations. Approximately 3-5% of electrodes from each MEA were excluded from further analysis due to the presence of noise. We analyzed two general measures of network function using the same prewhitened data, namely (a) the crosscorrelations, CC, between electrodes and (b) the simultaneous departure from equilibrium, SDE. With respect to the crosscorrelations, we analyzed (a) their sign (positive, negative) and its prevalence (e.g. positive/negative ratio), (b) their value, and (c) the relations of these measures to the lag, DIV and distance between electrodes. For the SDE, we analyzed its evolution with DIV and its relations to the strength of the average absolute value to the crosscorrelation.

3.2. Crosscorrelations

Figure 4:
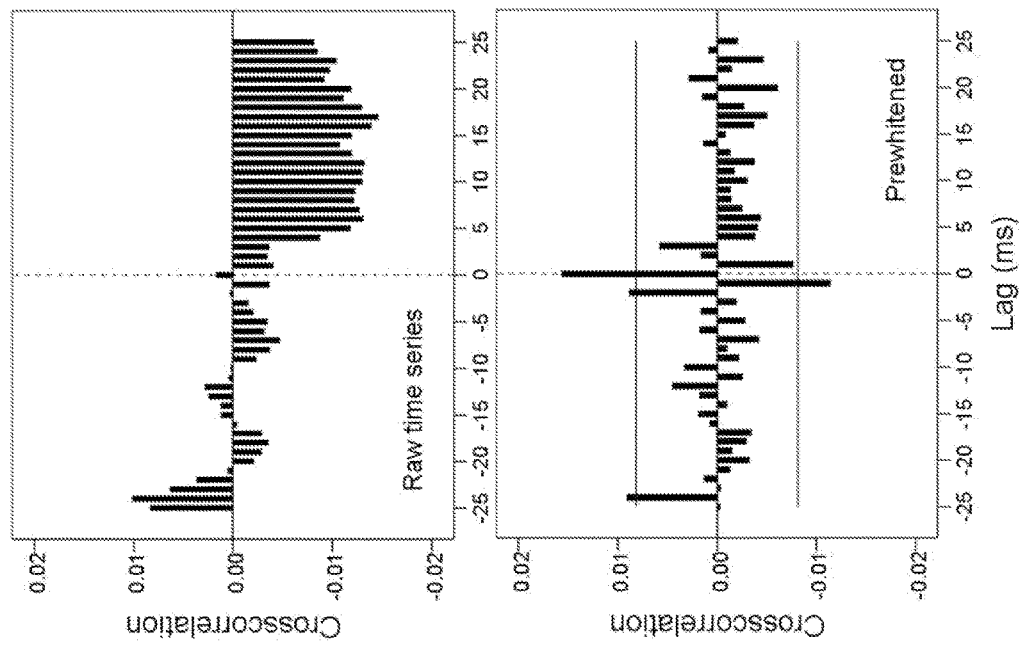
FIG. 4 is a diagram illustrating two crosscorrelograms of the same pair of LFP series plotted before (raw) and after prewhitening of the time series using an ARIMA (25,1,1) model. The crosscorrelogram computed from the raw data is spurious (top panel), whereas the one computed from pre-whitened data is correct (bottom panel). Horizontal lines indicate 95% confidence intervals for the crosscorrelation.

FIG. 4 illustrates the effects of prewhitening of the LFP time series on the crosscorrelations computed. The top and bottom panels plot the crosscorrelograms computed from the raw and prewhitened LFP time series, respectively. The two crosscorrelograms are drastically different; the upper one is spurious, whereas the bottom one is correct. This result highlights the importance of prewhitening for the crosscorrelation analysis. The findings below were obtained using prewhitened data. Since the findings were very similar across the four MEAs, final analyses were done on pooled data from all four MEAs.

3.2.1. Sign of Crosscorrelations

Figure 5:
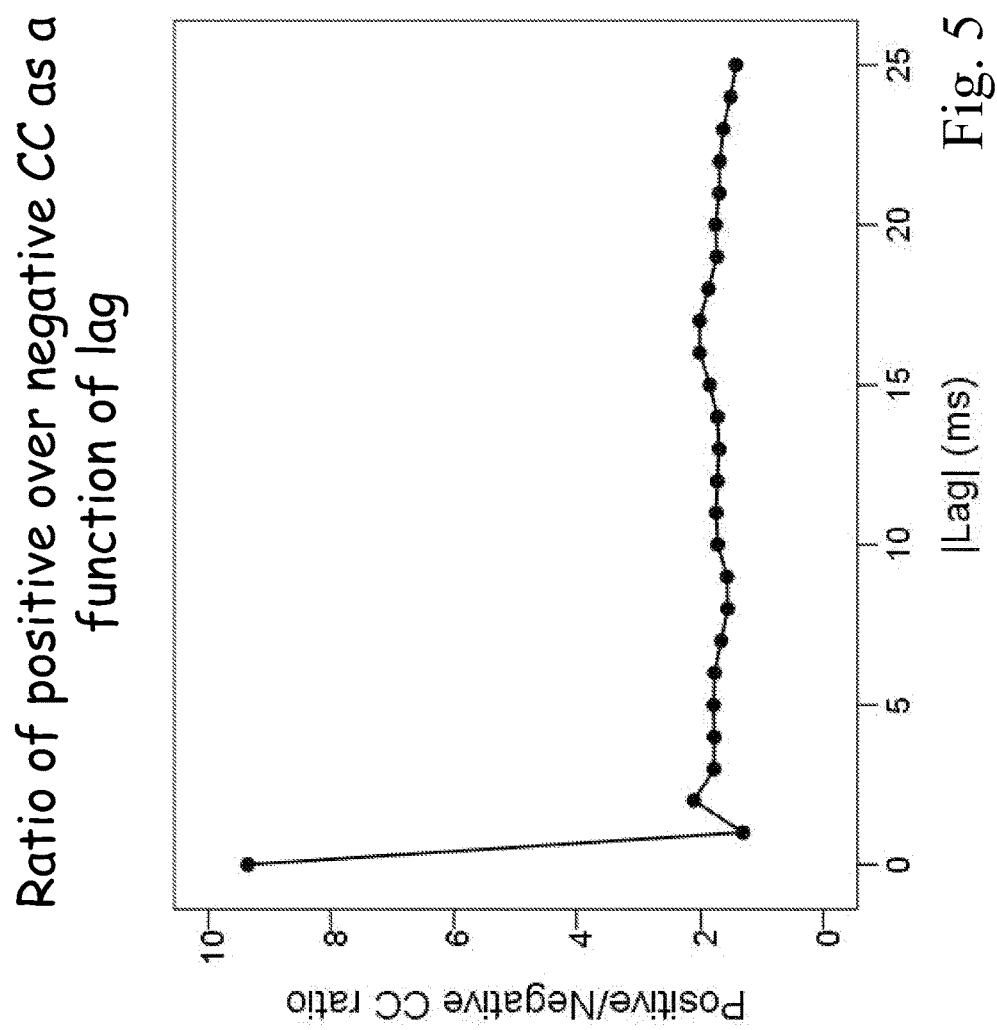
FIG. 5 is a diagram illustrating the positive/negative CC ratio (averaged across electrode pairs and DIV) plotted against |lag|. The ratio is much higher at zero lag.

A total of 10,377,429 cross correlations were computed. Overall, positive crosscorrelations were more prevalent than negative ones (63.8% vs. 36.2%, respectively). However, this prevalence was much higher at zero lag (90.3% vs. 9.7%), and lower at the other lags (positive: 63.3%±0.48, mean±SEM; negative: 36.7%±0.48, N=25 absolute lags). The positive/negative ratio was 9.35 for zero lag and an average of 1.73 for the other lags (FIG. 5). FIG. 5 shows the ratio of positive over negative CC as a function of lag. In addition, this ratio varied with DIV, and in a very different manner, depending on the lag. For zero lag, it decreased dramatically in a power law fashion (FIG. 6, upper panel) according to the equation ($P<10^{-14}$, $r^2=0.838$):

$$\frac{pos}{neg} = 5220 \, DIV^{-2} \qquad \text{EQUATION VIII}$$

or, equivalently $$\ln\left(\frac{pos}{neg}\right) = 8.56 - 2.0\ln(DIV) \qquad \text{EQUATION IX}$$

Figure 6:
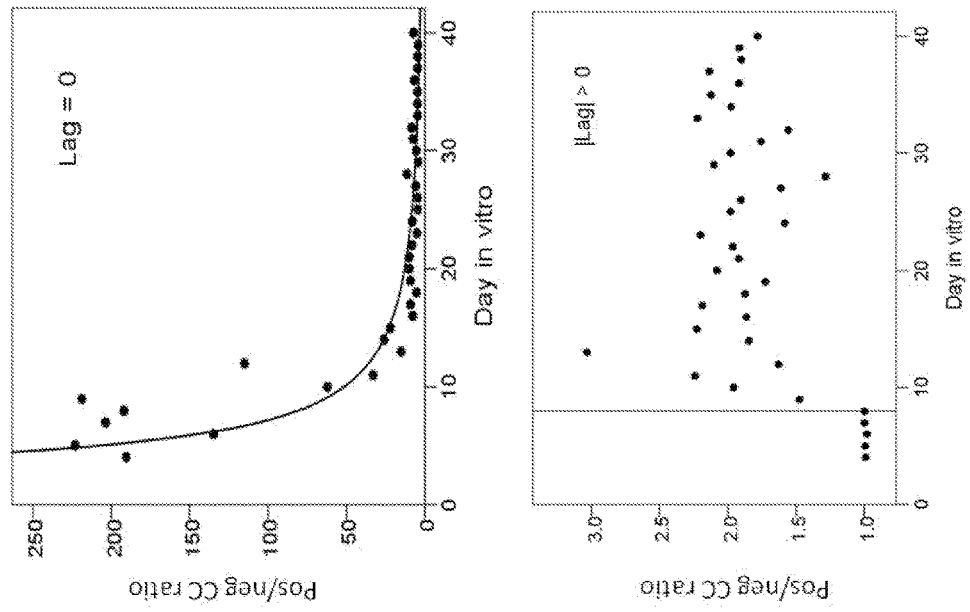
FIG. 6 is a diagram illustrating the positive/negative CC ratio (averaged across electrode pairs) plotted against DIV, separately for zero lag and averaged across |lag|>0.

In contrast, the positive/negative ratio for other lags was around 1 up to DIV 8, and then increased to about 2 for the remaining days (FIG. 6, lower panel); this was observed for all absolute lags greater than zero. FIG. 6 shows the ratio of pos/neg CC as a function of DIV.

Figure 7:
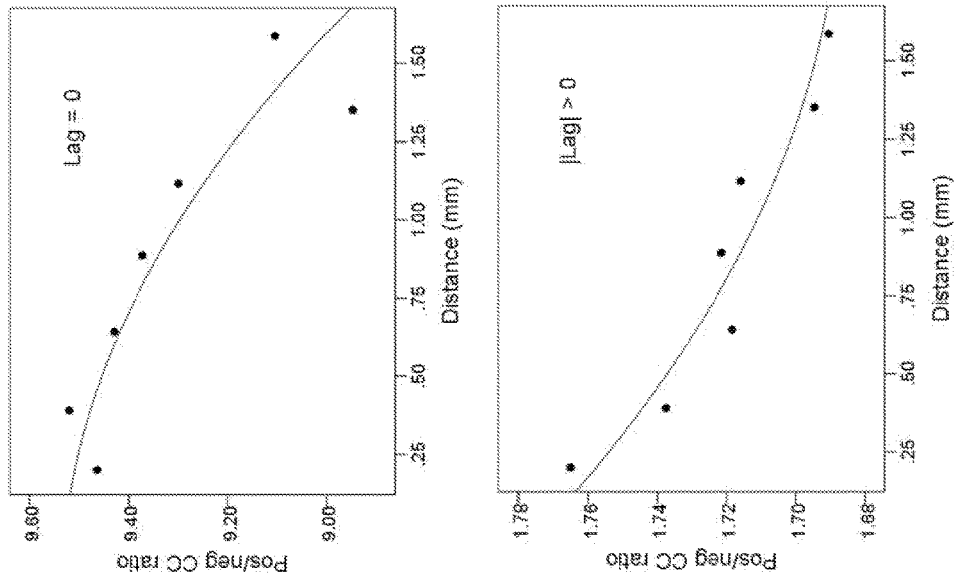
FIG. 7 is a diagram illustrating the positive/negative CC ratio (averaged across electrode pairs and DIV) decreased with inter-electrode distance both for zero lag and for |lag|>0.

Finally, the positive/negative CCF ratio also declined as a quadratic function of the distance between electrodes but in a different fashion for zero and nonzero lags (FIG. 7). FIG. 7 shows how the ratio of pos/neg CC drops with interelectrode distance.

3.2.2. Magnitude of Crosscorrelations

Figure 8:
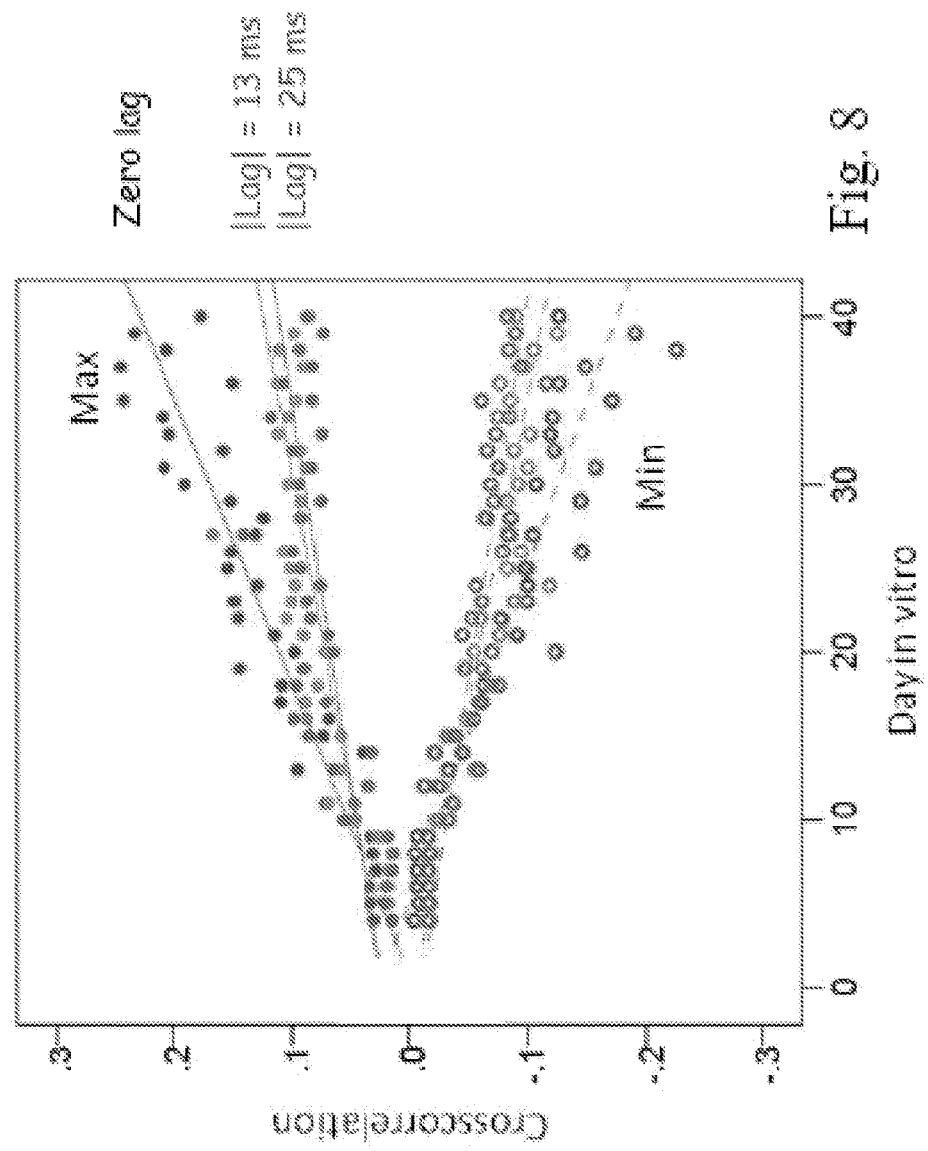
FIG. 8 is a diagram illustrating maximum (filled circles) and minimum (open circles) crosscorrelations (over electrode pairs) plotted against DIV for three lags: 0 ms, 13 ms, and 25 ms. Linear fit lines are also shown.
Figure 9:
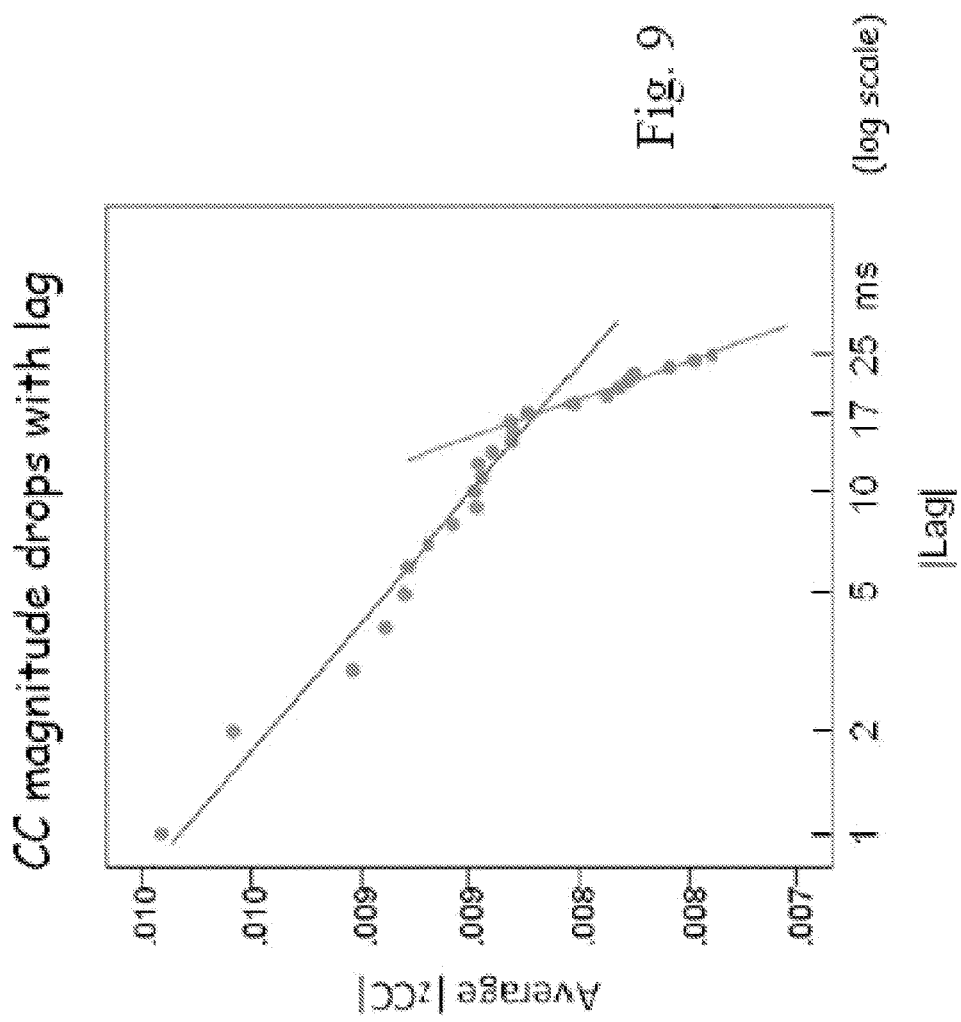
FIG. 9 is a diagram illustrating the average |zCC| (across electrode pairs and DIV) plotted against |lag|.
Figure 10:
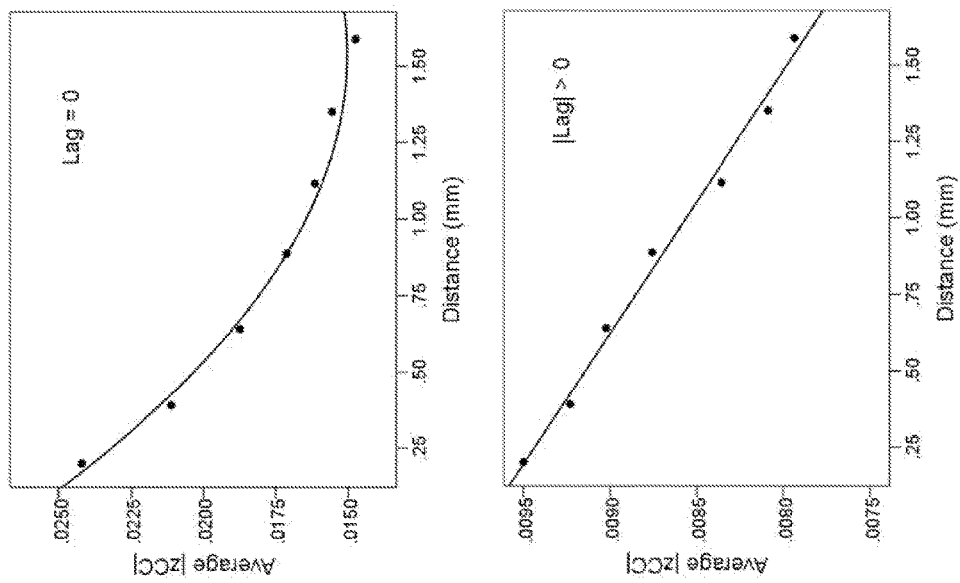
FIG. 10 is a diagram illustrating the average |zCC| (across electrode pairs and DIV) decreased with inter-electrode distance both for zero lag and for |lag|>0.

The magnitude of the crosscorrelation varied with DIV, the absolute lag (|lag|, or simply "lag"), and inter-electrode distance. With respect to DIV, the strength of crosscorrelations increased as the cultures grew. This held for all the lags. FIG. 8 plots maximum and minimum crosscorrelations against DIV for three lags (zero, 13 ms and 25 ms). It can be seen that the trend was more pronounced for the zero lag, as expected by the generally stronger correlations at that lag. With respect to the lag, both positive and negative crosscorrelations decreased in absolute value with increasing lag. FIG. 9 plots the average z-transformed crosscorrelation against the lag in a log scale (zero lag excluded). It can be seen that there is a break at |lag|=16 ms, such that later crosscorrelations fall at a steeper rate. Finally, the average absolute crosscorrelation decreased with inter-electrode distance (FIG. 10), indicating stronger interactions at short distances. FIG. 10 shows how the CC magnitude drops with interelectrode distance.

3.2.3. Partial Crosscorrelations

Figure 11:
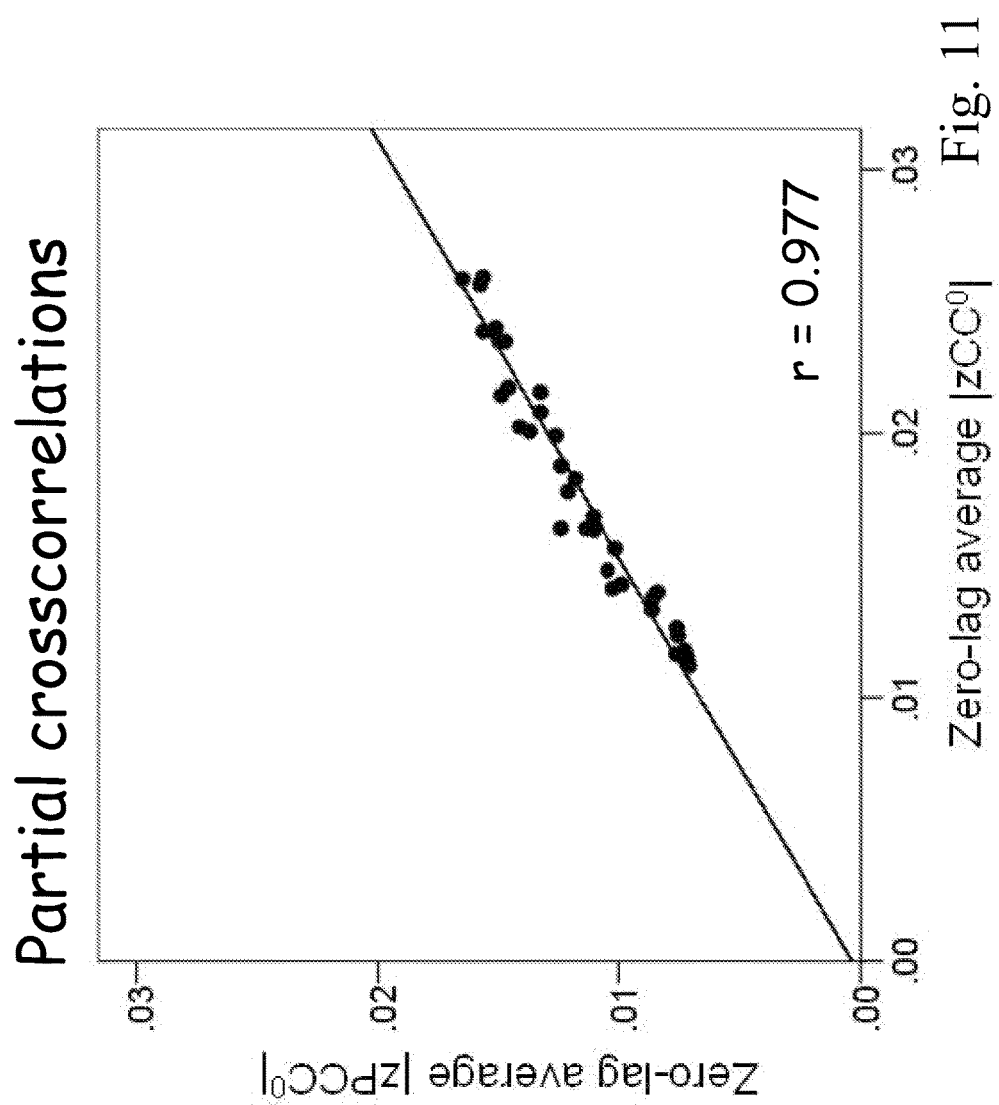
FIG. 11 is a diagram illustrating the average zero-lag partial crosscorrelation (across electrode pairs) plotted against the average (original) zero-lag crosscorrelation (N=37 days in vitro).

We also calculated the pairwise zero-lag partial correlations to account for potential correlations between electrodes in a pair and the other electrodes. As expected, the partial correlations were much lower magnitude (absolute value) than the original ones. FIG. 11 plots the average (across electrode pairs) absolute, zero-lag partial crosscorrelation against the original zero-lag cross correlation (N=37 days). It can be seen that the two are linearly related and that the partial correlation $|zPCC^0|$ is approximately 60% of the original $|zCC^0|$ ($r^2=0.955$, $P<10^{-24}$):

$$|zPCC^0|=0.0035+0.632|zCC^0| \qquad \text{EQUATION X}$$

It is also interesting that the line passes through the origin (the intercept of 0.0035 did not differ significantly from zero, linear regression, P=0.39). This means that average zero-lag partial crosscorrelations can be directly derived from average zero-lag crosscorrelations by simple scaling, i.e. x0.632.

3.3. Simultaneous Departure from Equilibrium

Figure 12:
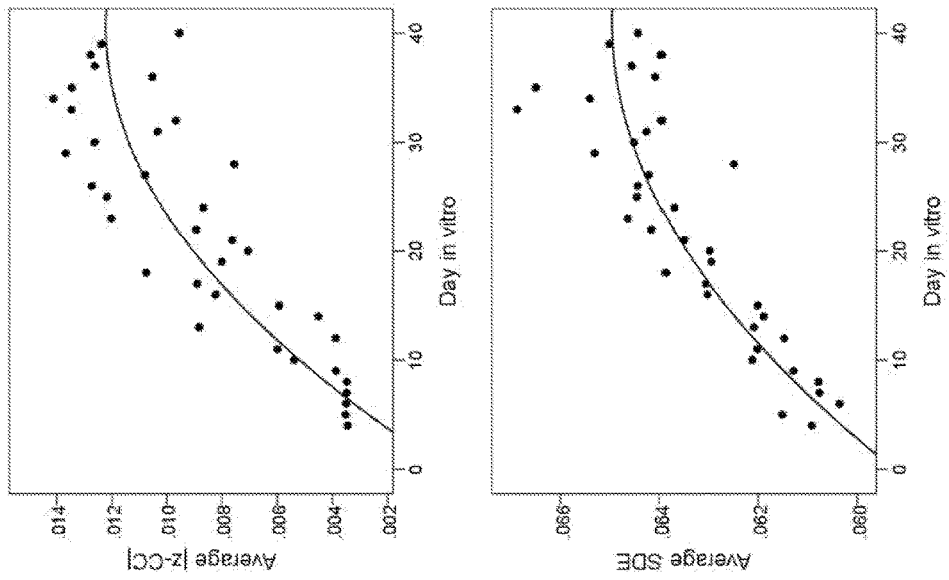
FIG. 12 is a diagram illustrating the average |zCC| and SDE increase with DIV.
Figure 13:
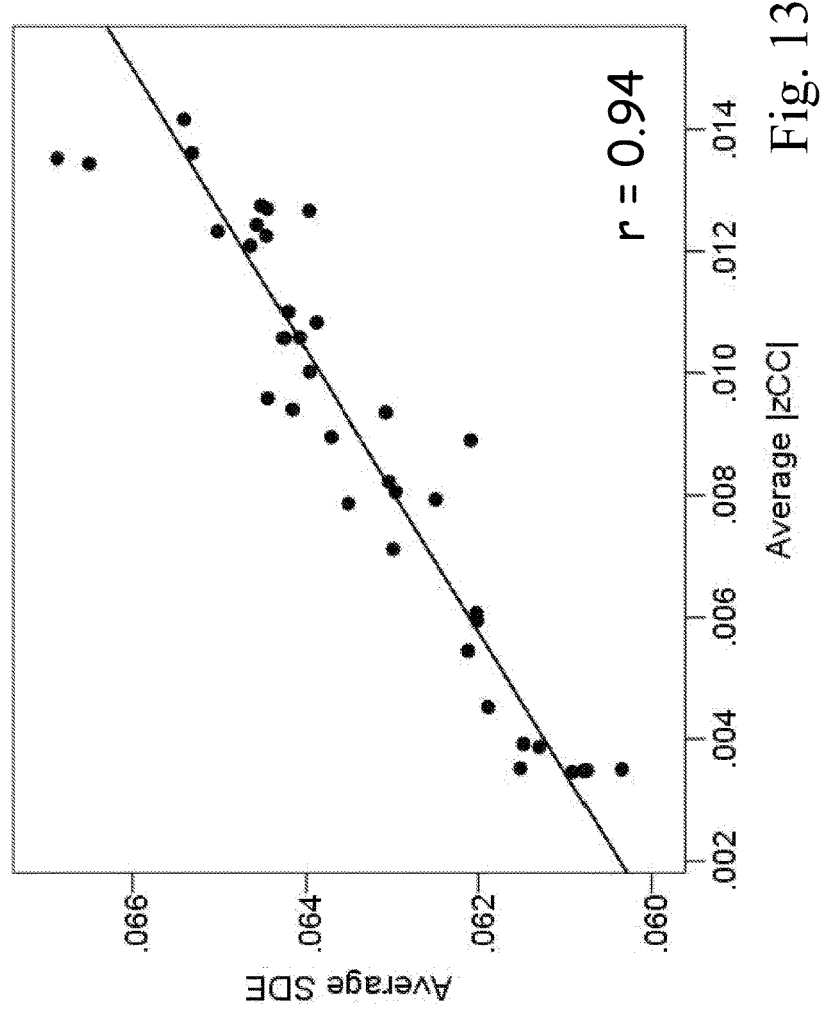
FIG. 13 is a diagram illustrating the average SDE plotted against the average (across all lags) |zCC| (N=37 DIVs).
Figure 14:
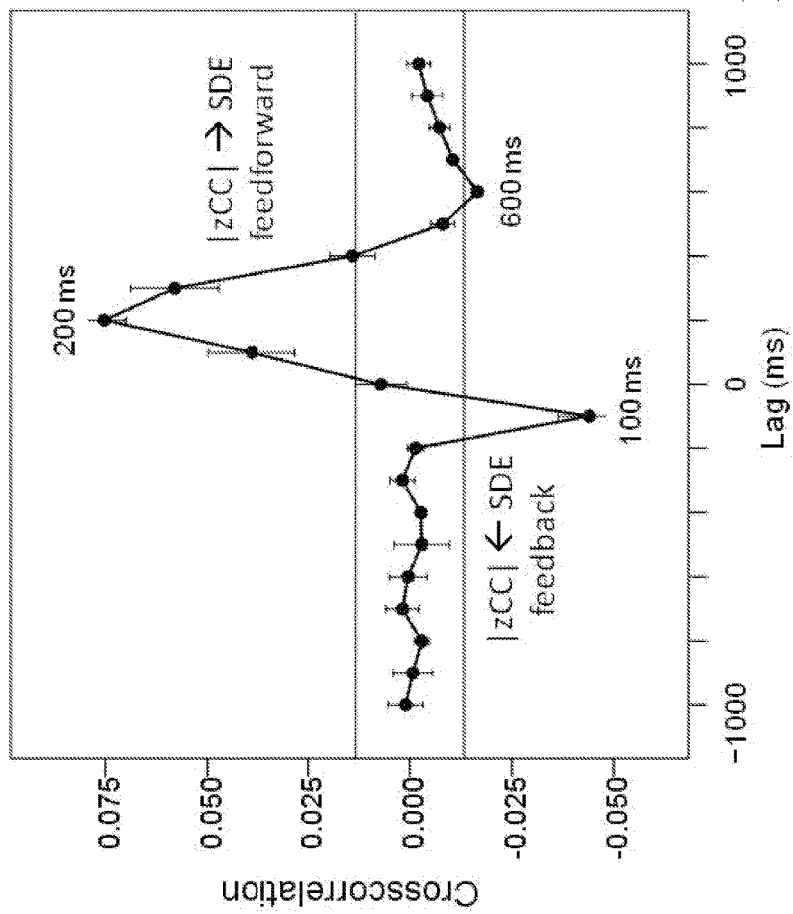
FIG. 14 is a diagram illustrating a crosscorrelogram between |zCC| and SDE computed from 100-ms long time periods. Error bars are SEM (N=4 MEAs).
Figure 15:
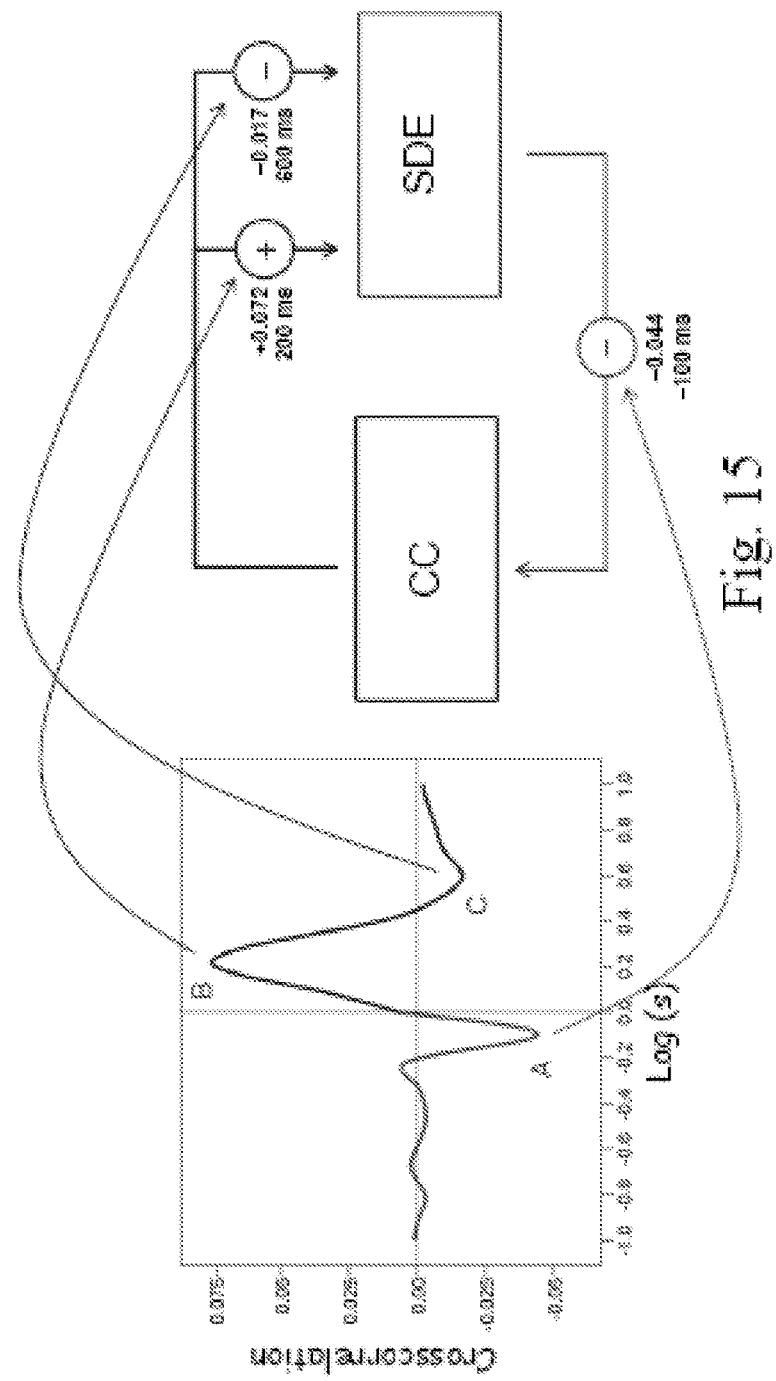
FIG. 15 is a diagram illustrating a crosscorrelogram (from FIG. 14) and schematic diagram to illustrate the feedforward and feedback relations between |zCC| and SDE.

FIG. 12 (lower panel) plots the time-varying average SDE against DIV. It can be seen that SDE increased in magnitude over time during the 37 days of recording (i.e. 40 DIV), indicating progressively larger fluctuations in synchronous departures from equilibrium. (Occasional consecutive maximum deviations from equilibrium, i.e. SDE=1, in a "bursting" pattern were observed at later days in vitro.) A very similar trend was also observed for the average (across all lags) crosscorrelation (FIG. 12, upper panel). In fact, the average SDE and average |zCC| were highly correlated (r=0.94, $P<10^{-17}$, N=37 days) (FIG. 13). FIG. 13 plots the average SDE versus the average |zCC|. This finding suggests that the pairwise synaptic interactions, as measured by the average crosscorrelation, might underlie the global fluctuations (SDE) at the network level at the macro-time scale, over 37 days of recording. We evaluated this hypothesis by calculating the SDE vs. |zCC| relation within a micro-time 100-ms scale and analyzing the relations between these two variables for each MEA at that temporal resolution. Specifically, we performed a crosscorrelation analysis to determine the temporal interactions between MEA |zCC| and SDE. Since the values came from temporal samples close together, we evaluated the |zCC| and SDE time series and found that there were significant autocorrelations suggesting an autoregressive process. Thus, we prewhitened the series by applying an ARIMA (25,1,1) model which yielded white noise innovations. We then calculated the crosscorrelations between these innovations for each MEA (±10 lags of 100-ms each) and found that all four MEAs gave very similar results. FIG. 14 shows the crosscorrelation function between |zCC| and SDE. It can be seen that the crosscorrelation function has a distinctive shape composed of (a) a sequence of prominent positive values with a peak at lag=+ 200 ms, followed by (b) a tail of negative values at lags>+ 500 ms, and (c) a negative peak at lag=−100 ms. These results indicate that |zCC| drives SDE with a delay-to-peak of 200 ms, followed by a mild rebound negative effect on SDE at later lags (>500 ms). In contrast, there is a short and sharp negative feedback from SDE to |zCC| within 100 ms. These feedforward and feedback relations are illustrated in the diagram of FIG. 15.

4. Discussion

In this work we analyzed in detail the interactions within neural networks recorded from brain cultures grown in vitro using multielectrode arrays. We carried out two levels of analysis, one using pairwise crosscorrelations up to ±25 lags (1-ms each), and another introducing a measure of network function based on the simultaneous departure from equilibrium SDE of constituent elements. We found systematic and significant relations between (a) the sign and magnitude of crosscorrelations on the one hand, and |lag|, day in vitro and inter-electrode distance on the other, (b) SDE and DIV, and (c) SDE and overall crosscorrelation strength, both across days in vitro and within 100-ms time bins. Overall, these results indicate an orderly and progressive dynamic development of neural network activity over many DIV. In addition, they validate the SDE as a measure of global network status and trace its relation to the overall crosscorrelation as a system with feedforward and feedback components.

4.1. Methodological Considerations

All the analyses in this work were done after the LFP time series were prewhitened following ARIMA modeling. Interactions assessed by crosscorrelations computed from integrated and/or autocorrelated time series are spurious.

4.2. Crosscorrelations

Properly calculated (i.e. non-spurious) crosscorrelations provide valuable information regarding dynamic relations in a network. The calculation of all pairwise crosscorrelations at ±25 lags with 1-ms temporal resolution yielded systematic relations within the developing neural network.

4.2.1. Sign of Crosscorrelations

First of all, positive crosscorrelations (across all days) substantially outnumbered negative correlations (FIG. 5), from ~9:1 at zero lag to ~2:1 for the other lags, in a practically constant fashion. The high prevalence of positive correlations at zero lag indicates a strong, highly temporally focused (1-ms) synchronicity, whereas the relatively constant ratio for all the other lags indicates a stable background organization of temporal network interactions. Remarkably, the positive/negative CC ratio changed very differently with DIV (FIG. 6), with respect to zero or greater lags, as follows. For zero lag, it started very large (>200 at day 4) and dropped precipitously during the subsequent days to stabilize at ~7.0 after day 20. In contrast, for |lag|>0, it was constant at a value of 1 for days 4-9, then jumped to an average of ~2 for the remaining days. These findings suggest that zero-lag synchronicity is a special case, and one that is subject to intense modification at the initial stages of growth. Finally, the change observed in the positive/negative CC ratio with inter-electrode distance (FIG. 7) is also interesting. For both zero lag and |lag|>0, this ratio decreased with distance, indicating a preponderance of positive interactions at short distances.

4.2.2. Magnitude of Crosscorrelation

The magnitude of crosscorrelation increased with DIV (FIG. 8), at all lags; positive correlations became more positive, and negative became more negative. Linear fits were adequate, with the slope decreasing with the lag (FIG. 8). These findings document the systematic increase and spread (over lags) of synaptic interactions with culture growth. The average (across days) absolute crosscorrelation decreased with |lag| in a semi-log(FIG. 9). It is interesting that two lines gave the best fit, one from |lag|=1 to |lag|=16, and another with steeper slope from |lag|=17 to |lag|=25. Finally, the crosscorrelation decreased with inter-electrode distance (FIG. 10).

4.3. Simultaneous Departure from Equilibrium

SDE is a measure of global network fluctuations. Conceptually, it stems from the thermodynamic concept of equilibrium of a closed system. In our case, although there is neural growth, the 1-min duration of the recordings can be regarded too short for substantial growth to occur. In addition, since electrode time series are white noise, after prewhitening, they can also be regarded as being in temporal equilibrium. Therefore, at the network level, collective departures from equilibrium (in individual time series) can serve as a measure of global network fluctuations. Indeed, the results obtained document the utility of the SDE as a global network measure, as it increased systematically with DIV (FIG. 12, lower panel). More important, however, is the relation between SDE and CC, namely the fact that SDE is a linear function of CC. This finding was unexpected, for there is no obvious reason for which the total strength of synaptic interactions (reflected in the average |CC|) would affect systematic network departure from equilibrium. This consideration prompted us to examine the CC versus SDE relations at a much finer temporal scale to determine the presence of possible direct interactions and feedback mechanisms.

4.4. CC-SDE Interactions

For that purpose, we calculated the average |zCC| across ±25-ms lags in short time periods of 100-ms duration, for which we also computed the average SDE. This yielded |zCC| and SDE time series which enables us to analyze the temporal interactions between these two measures at a time resolution of 100 ms. Both of these series had significant autoregressive components, so they were prewhitened (separately for each MEA) using an ARIMA (25,1,1) model which yielded white noise innovations. Then a crosscorrelation analysis was performed (per MEA) between |zCC| and SDE. The results are shown in FIG. 14, which plots the crosscorrelation (mean±SEM, N=4 MEAs) for ±10 lags (100-ms each); positive lags indicate influence of |zCC| on SDE, whereas negative lags indicate influence of SDE on |zCC|. It can be seen that there are three clear peaks in this plot. At positive lags, there is a positive peak at 200 ms (100-400 ms duration), followed by a negative peak at 600 ms (450-1000 ms); these indicate delayed temporal effects of |zCC| on SDE. At negative lags, there is just one negative peak at −100 ms, indicating a negative feedback. These results suggest a feedforward-feedback system (FIG. 15), where pairwise synaptic interactions (measured by the average |zCC|) drive in a positive-negative sequence the global fluctuations of the network, which, in turn dampens the synaptic interactions with a short delay. The strongest effect is the positive drive of |zCC| on SDE (0.072; peak B in FIG. 15), which is ~4× stronger than the subsequent negative effect (−0.017; peak C) and ~2× stronger than the negative feedback (−0.044; peak A).

4.5. Concluding Remarks

The analyses performed in this study addressed directly neural network function at two separate levels, one at a fine grain of pairwise interactions between electrodes and another at a bird's eye view of the network with respect to its overall stability. The prewhitening of the electrode time series allowed for the correct assessment of pairwise interactions without spuriousness and, hence, for the estimation of the strength of these interactions using the crosscorrelation function. On the other hand, the simple counting of electrodes above or below their equilibrium activity yielded, in their ratio, a simple measure of network status. Now, these two measures (CC and SDE) are very different and without any similarity or overlap in their calculations; and yet, remarkably, they were highly correlated in "macro" time (days of brain culture in vitro; FIG. 13) and were systematically related in a feedforward-feedback manner in "micro" time (100 ms time bins; FIGS. 14 and 15). These results open new avenues in analyzing and assessing network function at different levels of organization and time scale, both for descriptive purposes as well as for the purpose of assessing effects of interventions (i.e. drugs) on network function. Finally, this approach is fairly general and can be formally extended to any network, with potentially useful applications to econometric, social, and other networks.

One embodiment is directed to a computer-implemented method for performing a functional assessment of a network. The network includes a plurality of interacting network elements. The method includes measuring a state of each of the elements at a plurality of time instances, thereby determining a plurality of state values associated with each of the elements. The method includes calculating for each element an associated median value representing a median of the state values associated with that element. The method includes identifying for each time instance a first total number of elements with an associated state value at that time instance that is above its median value, and a second total number of elements with an associated state value at that time instance that is below its median value. The method includes determining whether the network has departed from an equilibrium state based on the first total number and the second total number for each time instance. In one embodiment, the calculating, identifying, and determining are performed by at least one processor.

The determining whether the network has departed from an equilibrium state according to one embodiment includes calculating for each time instance a departure from equilibrium value based on the first total number and the second total number, wherein a magnitude of the departure from equilibrium value represents a distance of departure from equilibrium. The calculating for each time instance a departure from equilibrium value according to one embodiment includes dividing the first total number by the second total number, and calculating a logarithm of a result of the division. The calculating for each time instance a departure from equilibrium value according to one embodiment further includes adding a constant value to a result of the logarithm, thereby generating a sum, and calculating an absolute value of the sum.

In one embodiment, the network comprises at least a portion of a brain. In one form of this embodiment, the at least a portion of the brain comprises cultured brain tissue. In one embodiment the method includes measuring the state of the elements with a magnetoencephalography (MEG) device. In another embodiment, the method includes measuring the state of the elements with a multi-electrode array (MEA) device.

Another embodiment is directed to a system for performing a functional assessment of a network. The network includes a plurality of interacting network elements. The system includes a measurement unit configured to measure a state of each of the elements at a plurality of time instances, thereby determining a plurality of state values associated with each of the elements. The system includes a controller configured to calculate for each element an associated median value representing a median of the state values associated with that element, identify for each time instance a first total number of elements with an associated state value at that time instance that is above its median value, and a second total number of elements with an associated state value at that time instance that is below its median value, and determine whether the network has departed from an equilibrium state based on the first total number and the second total number for each time instance.

In one embodiment, the determining whether the network has departed from an equilibrium state includes performing with the controller a calculation of a departure from equilibrium value for each time instance based on the first total number and the second total number, wherein a magnitude of the departure from equilibrium value represents a distance of departure from equilibrium. In one embodiment, the performing with the controller a calculation of a departure from equilibrium value for each time instance includes dividing the first total number by the second total number, and calculating a logarithm of a result of the division. In one embodiment, the performing with the controller a calculation of a departure from equilibrium value for each time instance further includes adding a constant value to a result of the logarithm, thereby generating a sum, and calculating an absolute value of the sum.

The network according to one embodiment includes at least a portion of a brain. In one embodiment, the at least a portion of the brain includes cultured brain tissue. In one embodiment, the measurement unit comprises a magnetoencephalography (MEG) device. In another embodiment, the measurement unit comprises a multi-electrode array (MEA) device.

Yet another embodiment is directed to a computer-implemented method for performing a functional assessment of a brain. The brain includes a plurality of interacting network elements. The method includes measuring a state of each of the elements at a plurality of time instances, thereby determining a plurality of state values associated with each of the elements. The method includes calculating for each element an associated median value representing a median of the state values associated with that element. The method includes identifying for each time instance a first total number of elements with an associated state value at that time instance that is above its median value, and a second total number of elements with an associated state value at that time instance that is below its median value. The method includes determining whether the brain has departed from an equilibrium state based on the first total number and the second total number for each time instance.

In one embodiment, the method includes measuring the state of the elements with a magnetoencephalography (MEG) device. In another embodiment, the method includes measuring the state of the elements with a multi-electrode array (MEA) device.

Although the present disclosure has been described with reference to preferred embodiments, workers skilled in the art will recognize that changes can be made in form and detail without departing from the spirit and scope of the present disclosure.

What is claimed is:

1. A computer-implemented method for performing a functional assessment of a network, the network including a plurality of interacting network elements, the method comprising:
    measuring a state of each of the elements at a plurality of time instances with a network element state measurement unit, thereby determining a plurality of state values associated with each of the elements;
    calculating for each element an associated median value that is a median of the state values associated with that element;
    identifying for each of the time instances a first total number of the elements with an associated state value at that time instance that is above its associated median value, and a second total number of the elements with an associated state value at that time instance that is below its associated median value; and
    determining whether the network has departed from an equilibrium state based on the first total number and the second total number for each time instance, wherein determining whether the network has departed from an equilibrium state includes calculating for each time instance a departure from equilibrium value based on the first total number and the second total number, wherein a magnitude of the departure from equilibrium value represents a distance of departure from equilibrium, and wherein calculating for each time instance a departure from equilibrium value includes dividing the first total number by the second total number, and calculating a logarithm of a result of the division.

2. The method of claim 1, wherein the calculating, identifying, and determining are performed by at least one processor.

3. The method of claim 1, wherein calculating for each time instance a departure from equilibrium value further comprises:
 adding a constant value to a result of the logarithm, thereby generating a sum; and
 calculating an absolute value of the sum.

4. The method of claim 1, wherein the network comprises at least a portion of a brain.

5. The method of claim 1, wherein the network comprises cultured brain tissue.

6. The method of claim 1, wherein the network element state measurement unit comprises:
 a magnetoencephalography (MEG) device.

7. The method of claim 1, wherein the network element state measurement unit comprises:
 a multi-electrode array (MEA) device.

8. A system for performing a functional assessment of a network, the network including a plurality of interacting network elements, the system comprising:
 a network element state measurement unit to measure a state of each of the elements at a plurality of time instances, thereby determining a plurality of state values associated with each of the elements; and
 a controller configured to calculate for each element an associated median value that is a median of the state values associated with that element, identify for each of the time instances a first total number of the elements with an associated state value at that time instance that is above its associated median value, and a second total number of the elements with an associated state value at that time instance that is below its associated median value, and determine whether the network has departed from an equilibrium state based on the first total number and the second total number for each time instance, wherein determining whether the network has departed from an equilibrium state includes performing with the controller a calculation of a departure from equilibrium value for each time instance based on the first total number and the second total number, wherein a magnitude of the departure from equilibrium value represents a distance of departure from equilibrium, and wherein performing with the controller a calculating of a departure from equilibrium value for each time instance includes dividing the first total number by the second total number, and calculating a logarithm of a result of the division.

9. The system of claim 8, wherein performing with the controller a calculation of a departure from equilibrium value for each time instance further comprises:
 adding a constant value to a result of the logarithm, thereby generating a sum; and
 calculating an absolute value of the sum.

10. The system of claim 8, wherein the network comprises at least a portion of a brain.

11. The system of claim 8, wherein the network comprises cultured brain tissue.

12. The system of claim 8, wherein the network element state measurement unit comprises a magnetoencephalography (MEG) device.

13. The system of claim 8, wherein the network element state measurement unit comprises a multi-electrode array (MEA) device.

14. A computer-implemented method for performing a functional assessment of a brain, the brain including a plurality of interacting network elements, the method comprising:
 measuring a state of each of the elements at a plurality of time instances with a network element state measurement unit, thereby determining a plurality of state values associated with each of the elements;
 calculating for each element an associated median value that is a median of the state values associated with that element;
 identifying for each of the time instances a first total number of the elements with an associated state value at that time instance that is above its associated median value, and a second total number of the elements with an associated state value at that time instance that is below its associated median value; and
 determining whether the brain has departed from an equilibrium state based on the first total number and the second total number for each time instance, wherein determining whether the brain has departed from an equilibrium state includes calculating for each time instance a departure from equilibrium value based on the first total number and the second total number, wherein a magnitude of the departure from equilibrium value represents a distance of departure from equilibrium, and Wherein calculating for each time instance a departure from equilibrium value includes dividing the first total number by the second total number, and calculating a logarithm of a result of the division.

15. The method of claim 14, wherein the network element state measurement unit comprises:
 a magnetoencephalography (MEG) device.

16. The method of claim 14, wherein the network element state measurement unit comprises:
 a multi-electrode array (MEA) device.

* * * * *